(12) United States Patent
Menon et al.

(10) Patent No.: US 10,517,863 B2
(45) Date of Patent: Dec. 31, 2019

(54) TRILOBINE AND ITS NATURAL ANALOGS FOR USE AS A DRUG

(71) Applicants: PIERRE FABRE MEDICAMENT, Boulogne-Billancourt (FR); CENTRE NATIONAL DE LA RECHERCHE SCIENTIFIQUE (CNRS), Paris (FR)

(72) Inventors: Yoann Menon, Nailloux (FR); Christophe Long, Vielmur sur Agout (FR); François Sautel, Toulouse (FR); Paola B. Arimondo, Toulouse (FR)

(73) Assignees: PIERRE FABRE MEDICAMENT, Boulogne-Billancourt (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/765,040

(22) PCT Filed: Oct. 3, 2016

(86) PCT No.: PCT/EP2016/073580
§ 371 (c)(1),
(2) Date: Mar. 30, 2018

(87) PCT Pub. No.: WO2017/055632
PCT Pub. Date: Apr. 6, 2017

(65) Prior Publication Data
US 2018/0280379 A1 Oct. 4, 2018

(30) Foreign Application Priority Data
Oct. 2, 2015 (EP) ..................................... 15306555

(51) Int. Cl.
*A61K 31/4748* (2006.01)
*A61K 45/06* (2006.01)
*A61P 35/02* (2006.01)

(52) U.S. Cl.
CPC .......... *A61K 31/4748* (2013.01); *A61K 45/06* (2013.01); *A61P 35/02* (2018.01); *A61K 2300/00* (2013.01)

(58) Field of Classification Search
None
See application file for complete search history.

(56) References Cited

FOREIGN PATENT DOCUMENTS

JP 63-179826 A 7/1988

OTHER PUBLICATIONS

Ke et al., Medical Oncology (2011), vol. 28, S135-S141.*
Berman et al., "Regions of Focal DNA Hypermethylation and Long-range Hypomethylation in Colorectal Cancer Coincide with Nuclear Lamina-associated Domains," Nat Genet., vol. 44, No. 1, 2011, pp. 40-46 (17 pages total).
Ceccaldi et al., "C5-DNA Methyltransferase Inhibitors: From Screening to Effects on Zebrafish Embryo Development," ChemBioChem, 2011, (Published online Jun. 1, 2011), vol. 12, pp. 1337-1345.
Gros et al., "Development of a Universal Radioactive DNA Methyltransferase Inhibition Test for High-throughput Screening and Mechanistic Studies," Nucleic Acids Research, vol. 41, No. 19, 2013 (Published online Aug. 25, 2013), e185 pp. 1-12.
Gros et al., "DNA Methylation Inhibitors in Cancer: Recent and Future Approaches," Biochimie, vol. 94, 2012 (Available online Aug. 11, 2012), pp. 2280-2296.
Halby et al., "Rapid Synthesis of New DNMT Inhibitors Derivatives of Procainamide," ChemBioChem, vol. 13, 2012 (Published online Dec. 14, 2011), pp. 157-165.
Hall et al., "Multidrug-Resistance Modulators from *Stephania japonica*," J. Nat. Prod. vol. 60, No. 11, 1997 (Nov. 1997), pp. 1193-1195, XP002753562.
Hochedlinger et al., "Epigenetic Reprogramming and Induced Pluripotency," Development, vol. 136, No. 4, 2009 (Published online Jan. 23, 2009), pp. 509-523 (30 pages total).
Kelly et al., "Epigenetic Modifications as Therapeutic Targets," Nat Biotechnol., vol. 28, No. 10, Oct. 2010 (Available in PMC Apr. 1, 2012), pp. 1069-1078 (22 pages total).
Kelly et al., "Genome-wide Mapping of Nucleosome Positioning and DNA Methylation Within Individual DNA Molecules," Genome Research, vol. 22, 2012, pp. 2497-2506.
Klausmeyer et al., "Discovery and Preliminary SAR of Bisbenzylisoquinoline Alkaloids as Inducers of C/EBPα," Bioorganic & Medicinal Chemistry, vol. 20, No. 15, 2012 (Jun. 8, 2012), pp. 4646-4652, XP028428221.
Kuroda et al., "Antitumor Effect of Bisbenzylisoquinoline Alkaloids," Chem. Pharm. Bull. vol. 24, No. 10, Oct. 1976, pp. 2413-2420, XP002753563.
Miranda et al., "Methylation-Sensitive Single-Molecule Analysis of Chromatin Structure," Current Protocols in Molecular Biology, vol. 21, No. 17, Jan. 2010, pp. 21.17.1 to 21.17.16.
Pardo et al., "MethylViewer: Computational Analysis and Editing for Bisulfite Sequencing and Methyltransferase Accessibility Protocol for Individual Templates (MAPit) Projects," Nucleic Acids Research, vol. 39, No. 1, 2011 (Published online Oct. 19, 2010), e5 pp. 1-18.
Rohde et al., "BISMA—Fast and Accurate Bisulfite Sequencing Data Analysis of Individual Clones from Unique and Repetitive Sequences," BMC Bioinformatics, vol. 11, No. 230, 2010 (Published May 6, 2010) pp. 1-12.
Semwal et al., "The Genus *Stephania* (*Menispermaceae*): Chemical and Pharmacological Perspectives," Journal of Ethnopharmacology, vol. 132, No. 11, 2010 (Available online Aug. 27, 2010), pp. 369-383, XP027452985.
Sharma et al., "Epigenetics in Cancer," Carcinogenesis, vol. 31, No. 1, 2010 (Advance Access publication Sep. 13, 2009), pp. 27-36.
Written Opinion of the International Searching Authority and International Search Report (forms PCT/ISA/237 and PCT/ISA/210), dated Dec. 20, 2016, for International Application No. PCT/EP2016/073580.

* cited by examiner

*Primary Examiner* — Brian J Davis
(74) *Attorney, Agent, or Firm* — Birch, Stewart, Kolasch & Birch, LLP

(57) ABSTRACT

Trilobine and its natural triple-bridged bisbenzylisoquinoline alkaloidal analogues as DNMT inhibitors for use as a drug for the treatment of cancer and neurological diseases and for cell reprogramming, in particular to prime for chemotherapy or immunotherapy.

15 Claims, 1 Drawing Sheet
Specification includes a Sequence Listing.

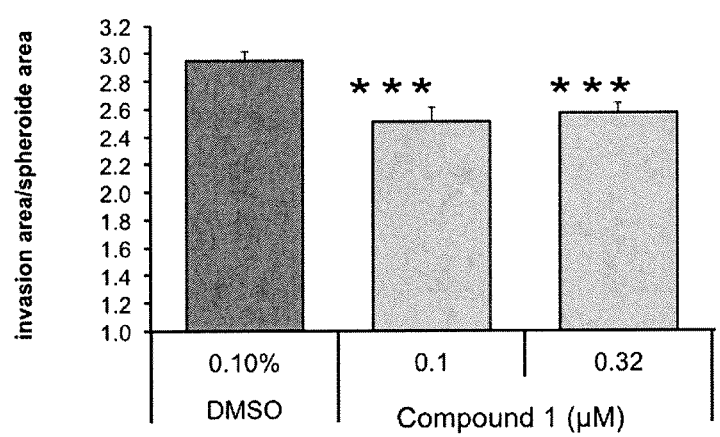

TRILOBINE AND ITS NATURAL ANALOGS FOR USE AS A DRUG

The present invention relates to trilobine and its natural analogues useful as DNA methyltransferase (DNMT) inhibitors, notably in the treatment of cancer.

Epigenetic modifications play an essential role in the establishment and regulation of differentiation programs that define when and where genes are expressed. Among these modifications, C5 methylation of deoxycytidines (dC) in the DNA was shown to play a key role in epigenetic regulation in mammals (Kelly et al. *Nature Biotech.* 2010, 28, 1069). It is the most stable epigenetic mark and occurs at position 5 of the cytosine ring within mainly CpG dinucleotides. The CpG sites are not distributed randomly across the human genome: they can be regrouped in islands, which are essentially located in promoters, present as repeated sequences, or located in CpG island shores (Gros et al. *Biochimie* 2012, 94, 2280). Hypermethylation of CpG islands located in promoters induces gene silencing while hypomethylation induces gene expression. Most of the CpG sites in the repetitive sequences are methylated, thus preventing chromosomal instability by silencing transposable DNA elements. Furthermore, some CpG island promoters become methylated in a sustainable manner during development, which results in turning gene expression off, a phenomenon observed in X-chromosome inactivation, imprinted genes and developmental genes. Methylation status of the promoters regulates dynamically gene expression through modification of the recognition by transcription factors and the proteins involved in chromatin remodeling.

DNA methyltransferases (DNMTs) catalyse the transfer of a methyl group from S-adenosyl-L-methionine (SAM) to position 5 of the cytosine at the CpG site. Two families of catalytically active DNMTs have been identified: DNMT1, responsible for DNA methylation maintenance during replication, and DNMT3A and 3B, responsible for de novo DNA methylation.

Alteration of DNA methylation patterns leads to various diseases such as cancer and neurological diseases. Cancerous cells present aberrant DNA methylation. In particular, a specific hypermethylation of tumour suppressor genes is observed, inducing their silencing. Restoring their expression by specific inhibition of DNA methylation represents an attractive therapeutic strategy. In addition, it has been shown that demethylating agents prime cancer cells towards immunotherapy and sensitize them towards chemotherapy.

DNMT inhibitors can be divided into two families: nucleoside analogues and non-nucleosides. The first are the most active ones. Two of them are FDA approved: 5-azacytidine (Vidaza® or 5azaC) and 5-azadeoxycytidine (Dacogene® or 5azadC). Despite their high efficiency, their poor bioavailability, their instability in physiologic media and their little selectivity restrict their use. Non-nucleoside analogues present various structures and mechanisms of action. Many of them were shown to target the catalytic site but suffer from lack of specificity and weak activity.

There exists thus a need for novel DNMT inhibitors.

The inventors of the present invention have thus discovered that natural triple-bridged bisbenzylisoquinoline alkaloids trilobine and natural analogues can be used as DNMT inhibitors. Indeed, in their search of new DNMT inhibitors they discovered that in the natural extracts of *Cocculus hirsutus* were present potent inhibitors of DNA methylation able to express, in leukaemia KG-1 cells, the luciferase gene under the control of a methylated CMV promoter upon demethylation of the promoter and chromatin decompaction.

By a phytochemical approach, natural bisbenzylisoquinoline alkaloid trilobine and natural analogues were identified to be responsible of the biological activity. The inventors further characterized their ability to inhibit the DNMTs, to demethylate gene promoters and to induce chromatin opening.

The present invention concerns thus Trilobine and its natural triple-bridged bisbenzylisoquinoline alkaloidal analogues for use as a drug for the treatment of cancer and neurological diseases, in particular cancer.

The expression "natural" according to the invention refers to molecules that can be obtained for example from *Cocculus hirsutus*. The compounds according to the present invention can be obtained from the plant by methods well known to the one skilled in the art, such as by extraction followed by chromatography on a column of silica gel, high performance liquid chromatography (HPLC), evaporation of the solvent, or precipitation, distillation or crystallisation (followed by filtration) of the compound, and notably as described in example 1 of the present application.

In one embodiment, the trilobine and its natural triple-bridged bisbenzylisoquinoline alkaloid analogues are characterized in that they correspond to the following formula (I),

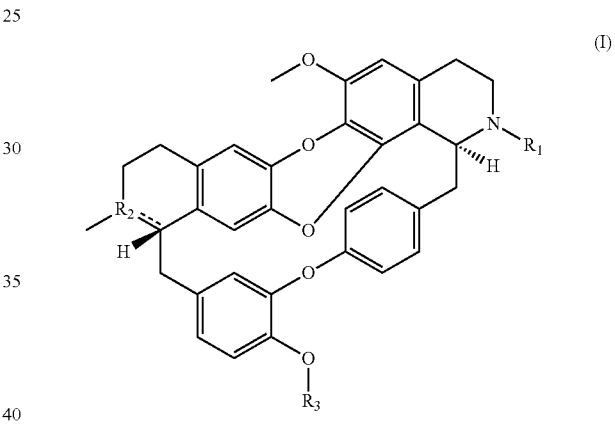

wherein:
$=$ represents a double or single bond,
$R_1$, $R_2$ and $R_3$ represent a hydrogen atom or a methyl group, at least one of said radicals $R_1$, $R_2$ and $R_3$ being a methyl group, or
$R_1$ and $R_3$ are independently one from the other a hydrogen atom or a methyl group and $R_2$ forms with the vicinal carbon atom in position 1 a double bond C=N, or a pharmaceutically acceptable salt or solvate thereof.

This means that:
when $=$ represents a single bond, $R_1$, $R_2$ and $R_3$ represent, independently of each other, a hydrogen atom or a methyl group, at least one of said radicals $R_1$, $R_2$ and $R_3$ being a methyl group,
when $=$ represents a double bond, $R_1$ and $R_3$ are, independently of each other, a hydrogen atom or a methyl group, and $R_2$ is absent.

In one embodiment,
when $R_2$ is a methyl group, both $R_1$ and $R_3$ are hydrogen atoms, and
when $R_2$ is a hydrogen atom, at least one of $R_1$ and $R_3$ is a hydrogen atom.

In another embodiment, the trilobine and its natural triple-bridged bisbenzylisoquinoline alkaloid analogues according to the invention are selected from the group consisting of the compounds cited in table 1.

TABLE 1
trilobine and its natural triple-bridged
bisbenzylisoquinoline alkaloid analogues
| Ref. | Name |
|------|------|
| 1 | Trilobine |
| 2 | Isotrilobine |
| 3 | O-Methylcocsoline |
| 4 | Cocsuline |
| 5 | 2'-Norcocsuline |
| 6 | Cocsoline |
| 7 | Nortrilobine |
| 8 | 1,2-Dehydroapateline |
| 9 | 1,2-Dehydrotelobine |
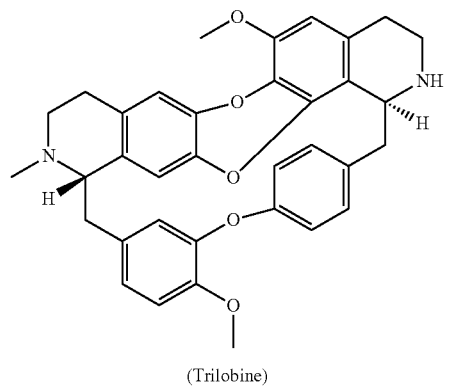
(Trilobine)
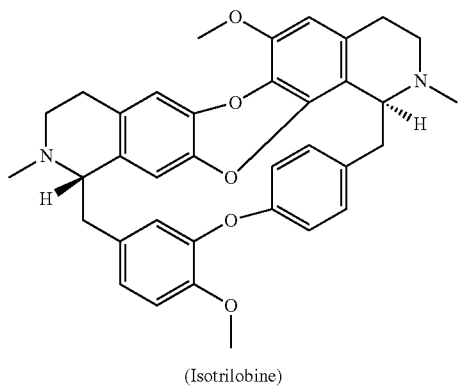
(Isotrilobine)
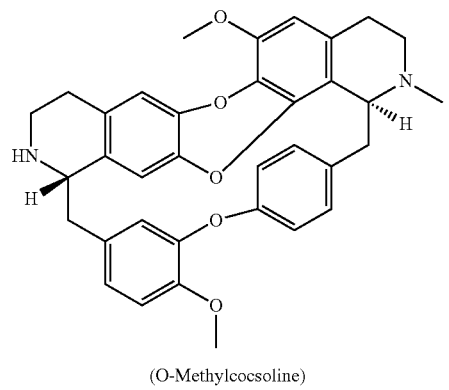
(O-Methylcocsoline)
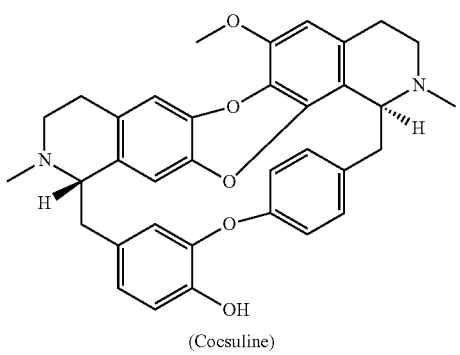
(Cocsuline)
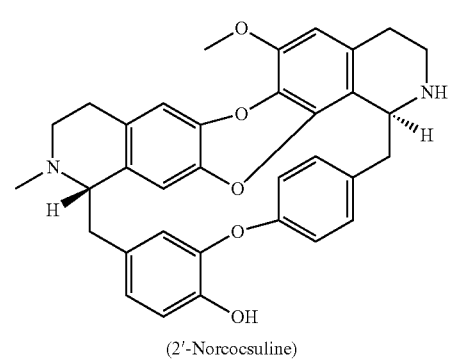
(2'-Norcocsuline)
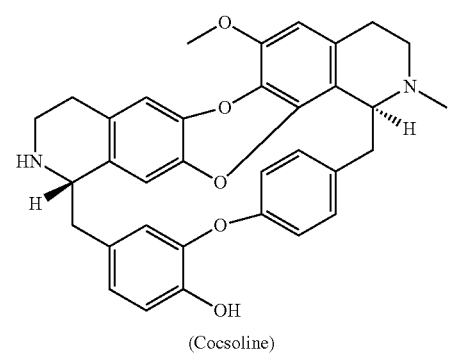
(Cocsoline)
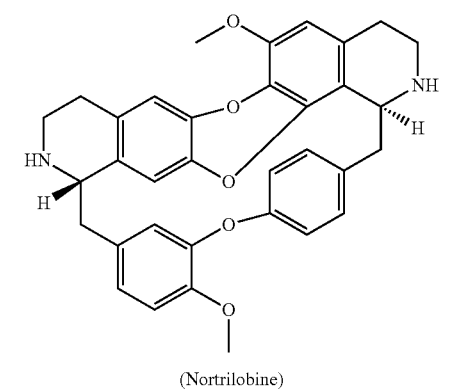
(Nortrilobine)

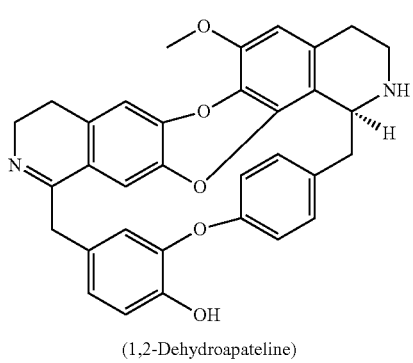

(1,2-Dehydroapateline)

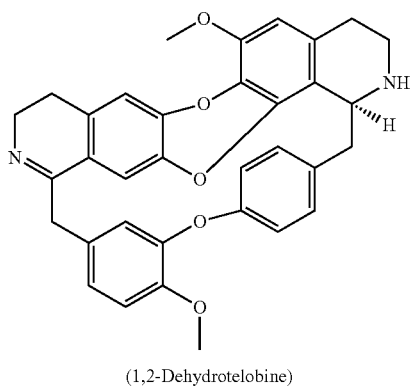

(1,2-Dehydrotelobine)

The pharmaceutically acceptable salts and solvates thereof fall also within the scope of the present invention.

In another embodiment of the invention, the trilobine and its natural triple-bridged bisbenzylisoquinoline alkaloid analogues are selected from the group consisting of O-methylcocsoline, cocsuline, 2'-norcocsuline, cocsoline, nortrilobine, 1,2-dehydroapateline, 1,2-dehydrotelobine, and the pharmaceutically acceptable salts and solvates thereof.

In one embodiment, the trilobine and its natural triple-bridged bisbenzylisoquinoline alkaloide analogues are DNA methyl transferase (DNMT) inhibitors.

Consequently, the invention concerns also the trilobine and its natural triple-bridged bisbenzylisoquinoline alkaloide analogues as defined previously for use as DNMT inhibitors.

According to the invention, the expression "DNMT inhibitors" refers to molecules that are able to reduce the DNA methyltransferase activity. Preferentially, the use of a DNMT inhibitor according to the invention makes it possible to inhibit the activity of said DNMT. The compounds showed also their properties of inhibitors of DNA methylation in cells. The DNMT inhibitory activity can be tested by measuring the expression of a CMV-Luc gene, notably as described in example II.1 of the present application, or by measuring the inhibition of hDNMT3A or hDNMT1 enzymes, notably as described in example II.2 and II.3 of the present application. DNMT inhibitors according to the invention are thus able to reprogram cells towards less aggressive states.

The present invention also relates to the use of Trilobine and its natural triple-bridged bisbenzylisoquinoline alkaloidal analogues according to the invention, for the manufacture of a drug, notably intended for the treatment of cancer, and neurological diseases.

The invention relates also to the use of Trilobine and its natural triple-bridged bisbenzylisoquinoline alkaloidal analogues for the manufacture of a drug intended for inhibiting DNMT.

The present invention also relates to a method for the treatment of cancer and neurological diseases comprising the administration to a person in need thereof of an effective dose of a compound selected from Trilobine and its natural triple-bridged bisbenzylisoquinoline alkaloidal analogues according to the invention.

The invention relates also to a method for inhibiting DNMT comprising the administration to a person in need thereof of an effective dose of a compound chosen among Trilobine and its natural triple-bridged bisbenzylisoquinoline alkaloidal analogues.

The neurological disease according to the invention may be more particularly schizophrenia and neurodegenerative diseases.

The cancer according to the invention may be colon cancer; hepatocarcinoma; melanoma; breast cancer; ovarian cancer; kidney cancer; liver cancer; pancreatic cancer; prostate cancer; glioblastoma; lung cancer, such as non-small cell lung cancer; neuroblastoma; myofibroblastic tumor; lymphoma, such as B- and T-cell lymphoma or anaplastic large-cell lymphoma; leukemia, such as AML (acute myeloid leukemia), MDS (myelodysplastic syndrome), CMML (chronic myelomonocytic leukemia) and CML (chronic myeloid leukemia); and multiple myeloma.

In particular, the cancer according to the invention may be colon cancer, hepatocarcinoma, melanoma, breast cancer, kidney cancer, liver cancer, pancreatic cancer, prostate cancer, glioblastoma, non-small cell lung cancer, neuroblastoma, myofibroblastic tumor, B- and T-cell lymphoma or anaplastic large-cell lymphoma, leukemia (AML, MDS, CMML, CML), multiple myeloma.

The cancer can be in particular a DNMT-overexpressing cancer.

As previously stated, cancerous cells can be characterized by a specific hypermethylation of tumor suppressor genes, which can result from an over-activation of DNMTs. Since the hypermethylation of tumor suppressor genes induces their silencing, the survival and proliferation of said tumor is dependent on the DNMTs activity. Inhibiting DNMTS results in a marked antitumor efficacy against tumors whose survival and proliferation is enabled by the overexpression of DNMTs.

In other words, overexpression of DNMTs may favour the growth and maintenance of various cancers irrespective of the nature and localization of the tumors. These tumors, in turn, are expected to be responsive to a treatment aiming to inhibit the overexpressed DNMT, which would results in the death of the tumoral cells.

By «overexpression» is meant in the context of the invention that the expression level of DNMT in a cancerous cell is higher than the reference expression level in a non cancerous cell. Preferentially, the reference expression level of DNMT is measured in a non cancerous cell of the same type as the cancerous cell. For example, when the cancerous cell is a colon cell, the non cancerous cell used for the measurement of the reference expression level will also be a colon cell. In a preferred embodiment, the level of expression of DNMT in a cancerous cell and the reference expression level in a non cancerous cell are measured in cells isolated from the same patient. In another embodiment, the reference expression level is the average of expression levels measured in non cancerous cells of several individuals.

The isolation of cancerous and non cancerous cell from a patient can be achieved by any technique known by the person skilled in the art and more specifically by biopsy.

In a first embodiment, if the non cancerous cells do not express DNMT (reference expression level egal 0), a higher level of expression means any observed level of expression. In a second embodiment, when the non cancerous cells express DNMT (reference expression level superior to 0) a higher level of expression mean any significant increase in the expression of DNMT according to the invention, for example an increase above or equal to 5%, notably above or equal to 10%, notably above or equal to 30%, notably above or equal to 50%, advantageously above or equal to 100%.

The level of expression of DNMT may be measured by any method known by the person skilled in the art for example by RT-PCR (reverse-transcription-based polymerase chain reaction), immunofluorescence, or western blot.

The present invention also relates to a pharmaceutical composition comprising at least one compound of formula (I) such as defined above, and at least one pharmaceutically acceptable excipient.

The pharmaceutical compositions according to the invention may be formulated notably for oral administration, topical administration or for injection, wherein said compositions are intended for mammals, including humans.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. It may be necessary to use doses outside these ranges as determined by the person skilled in the art.

The pharmaceutical compositions according to the invention may further comprise at least one other active ingredient, such as an anticancer agent.

The present invention relates also to a pharmaceutical product comprising:
(i) at least one compound of formula (I) such as defined above, and
(ii) at least one other active ingredient, such as an anticancer agent,
as a combination product for simultaneous, separate or sequential use in the treatment of cancer, in particular cell reprogramming to prime for chemotherapy or immunotherapy.

The said other active ingredient can be selected from the group consisting of:
Cytotoxic agents such as doxorubicin, R-CHOP (Rituximab, Cyclophosphamide, Hydroxydaunorubicin, Oncovin, Prednisone or Prednisolone), PARP (Poly ADP Ribose Polymerase) inhibitors, etoposide, cisplatin, vinorelbine, vinflunine, bortezomib, etc.;
Other epigenetics drugs such as:
Inhibitors histone deacetylase (HDACi, such as inhibitors of HDAC 1 & 2)
Inhibitors of chromatin remodeler (such as CHD4)
Inhibitors of histone modifiers (such as demethylases JARDI1A/B or methylases EZH2);
Immunotherapies such as antiCTL4 or antiPD1.

The present invention also relates to a pharmaceutical composition such as defined above for use as a drug, notably intended for the treatment of cancer.

LEGEND OF THE FIGURE

The FIGURE: Fluorescent invasion area for spheroids in presence of DMSO or of 0.1 or 0.32 μM of compound 1.

EXAMPLES

The examples, which follow, illustrate the invention without limiting its scope in any way.

The following abbreviations have been used in the following examples.

| | |
|---|---|
| BSA: | Bovine Serum Albumine |
| CMV: | cytomegalovirus |
| DMSO: | Dimethylsulfoxide |
| DNMT: | C5 DNA methyltransferase |
| EDTA: | Ethylenediaminetetraacetic acid |
| EMEM: | Eagle's Minimum Essential Medium |
| HEPES: | 4-(2-Hydroxyethyl)-1-piperazineethanesulfonic acid |
| HPLC: | High Performance Liquid Chromatography |
| HRMS: | High Resolution Mass Spectrometry |
| luc: | luciferase |
| NMR: | Nuclear Magnetic Resonance |
| PBS: | Phosphate buffered saline |
| PBST: | Phosphate buffered saline + Tween-20 |
| PCR: | Polymerase Chain reaction |
| RT: | Room temperature |
| SAM: | S-adenosyl-L-methionine |
| TLC: | Thin Liquid Chromatography |

Example I. Obtention of the Compounds According to the Invention Extraction and Isolation The roots (1 kg) of *Cocculus hirsutus* (Menispermaceae) were powdered and extracted at room temperature with methanol (10 L) overnight (2 times). After filtration, the extract was concentrated under reduced pressure. The residue was partitioned between ethyl acetate and hydrochloric acid (10%, W/W). The aq. layer was alkalized (pH=9) with sodium carbonate and partitioned between dichloromethane and water. The organic layer was evaporated under reduced pressure to give 1.6 g of crude alkaloid mixture (yield 0.16%). Then the crude extract was subjected to silica gel column chromatography (40 g–125×25 mm–30 μm), with a gradient elution of dichloromethane-methanol (100:0 to 75:25) and 100% methanol to give 35 fractions of 30 mL. All the fractions were analyzed by TLC on silica gel using solvent mixture dichloromethane-methanol (90:10) and pooled according to TLC into 7 fractions (F1-F7). Fraction F2 (151 mg) was purified by semipreparative HPLC RP-18 Lichrospher (250×25 mm, 5 μm), eluting with a linear gradient of water-acetonitrile 0.02% triethylamine (30:70 to 0:100) to give 2 (125 mg). Fraction F3 (98 mg), fraction F4 (121 mg) and fraction F5 (103 mg) were purified by semipreparative HPLC RP-18 Lichrospher (250×25 mm, 5 μm), eluting with a linear gradient of water-acetonitrile 0.02% triethylamine (50:50 to 0:100) to give 4 (64 mg), 3 (65 mg) and 1 (100 mg). Fraction F6 (160 mg) and the fraction F7 (49 mg) were purified by semipreparative HPLC RP-18 (250×25 mm, 5 μm), eluting with a linear gradient of water-acetonitrile 0.02% triethylamine (80.20 to 0:100) to give 5 (34 mg), 6 (30 mg) and 7 (1 mg).

The roots (100 g) of *Cocculus orbiculatus* (Menispermaceae) were powdered and extracted at room temperature with methanol (1 L) overnight (2 times). After filtration, the extract was concentrated under reduced pressure. The residue was partitioned between ethyl acetate and hydrochloric acid (10%, W/W). The aq. layer was alkalized (pH=9) with sodium carbonate and partitioned between dichloromethane and water. The organic layer was evaporated under reduced pressure to give 217 mg of crude alkaloid mixture (yield 0.22%). Then the crude extract was subjected to silica gel column chromatography (25 g–133×21 mm–30 μm), with a gradient elution of dichloromethane-methanol (100:0 to 85:15) and 100% methanol; to give 28 fractions of 30 mL. All the fractions were analyzed by TLC on silica gel using solvent mixture dichloromethane-methanol (90:10) and pooled according to TLC into 5 fractions (F1-F5). Fraction F2 (27 mg) was purified by semipreparative HPLC RP-18 X-Terra (250×19 mm, 5 μm), eluting with a linear gradient of water-acetonitrile 0.02% triethylamine (20:80 to 0:100) to give 8 (4.6 mg), 9 (0.5 mg), 1 (1.5 mg) and 2 (1.4 mg).

The following compounds were obtained.

Trilobine (1)

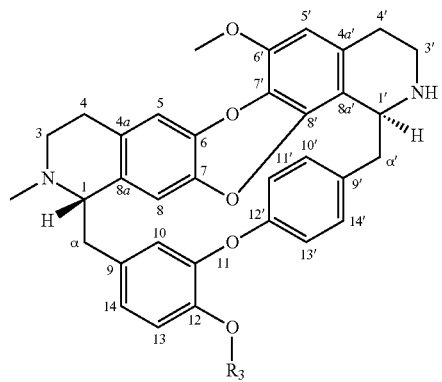

(1)

$^1$H NMR (500 MHz, MeOD) δ 7.64 (1H, dd, J=8.3 Hz, J=1.9 Hz, H-14'), 7.15 (2H, m, H-10', H-13'), 6.96 (1H, d, J=8.3 Hz, H-13), 6.93 (1H, dd, J=8.3 Hz, J=2.7 Hz, H-11'), 6.87 (1H, dd, J=8.1 Hz, J=2.0 Hz, H-14), 6.52 (1H, s, H-5), 6.49 (1H, d, J=2.0, H-10), 6.43 (1H, s, H-5'), 6.07 (1H, s, H-8), 4.27 (1H, t, J=3.3 Hz, H-1'), 3.92 (3H, s, 12-OMe), 3.78 (3H, s, 6'-OMe), 3.27 (1H, m, H-α'), 3.22 (1H, m, H-1), 3.15-3.10 (2H, m, H-3'), 2.92-2.56 (9H, m, H-3, H-4, H-4', H-α, H-α'), 2.39 (3H, s, N2-Me).

$^{13}$C NMR (125 MHz, MeOD) δ 155.7 (C-12'), 151.8 (C-11), 148.8 (C-12), 147.8 (C-6'), 141.2 (C-6 or C-7 or C-9'), 141.0 (C-6 or C-7 or C-9'), 140.1 (C-8'), 136.4 (C-9), 136.2 (C-8a), 132.5 (C-10'), 131.0 (C-4a), 130.8 (C-7'), 129.8 (C-4a'), 129.6 (C-14'), 123.5 (C-13'), 123.2 (C-14), 122.8 (C-11'), 122.4 (C-8a'), 118.3 (C-10), 116.7 (C-5), 115.3 (C-8), 114.1 (C-13), 108.4 (C-5'), 68.8 (C-1), 56.9 (C-6'-OMe), 56.8 (C-12-OMe), 54.7 (C-1'), 50.5 (C-3), 45.6 (C-α'), 42.9 (C—N2-Me), 41.9 (C-α'), 39.3 (C-3'), 28.7 (C-4'), 28.1 (C-4).

HRMS-ESI (m/z) calculated for $C_{35}H_{35}N_2O_5$ [M+H]$^+$: 563.2540; Found: 563.2541.

Trilobine (2)

(2)

$^1$H NMR (500 MHz, MeOD) δ 7.63 (1H, dd, J=8.4 Hz, J=2.0 Hz, H-14'), 7.18 (1H, dd, J=7.8 Hz, J=2.0 Hz, H-10'), 7.16 (1H, dd, J=8.2 Hz, J=2.5 Hz, H-13'), 6.98 (1H, d, J=8.3 Hz, H-13), 6.95 (1H, dd, J=8.2 Hz, J=2.8 Hz, H-11'), 6.91 (1H, dd, J=8.3 Hz, J=2.0 Hz, H-14), 6.58 (1H, s, H-5), 6.56 (1H, d, J=1.9, H-10), 6.49 (1H, s, H-5'), 6.13 (1H, s, H-8), 4.10 (1H, m, H-1'), 3.93 (3H, s, 12-OMe), 3.83 (3H, s, 6'-OMe), 3.35 (1H, m, H-α'), 3.21 (1H, m, H-1), 3.17 (H, m, H-3'), 3.00-2.88 (4H, m, H-3, H-3', H-4', H-α), 2.81-2.60 (5H, H-3, H-4, H-4', H-α, H-α'), 2.57 (3H, s, N2'-Me), 2.37 (3H, s, N2-Me).

$^{13}$C NMR (125 MHz, MeOD) δ 156.0 (C-12'), 151.9 (C-11), 148.9 (C-12), 148.0 (C-6'), 141.4 (C-6 or C-7 or C-8' or C-9'), 141.0 (C-6 or C-7 or C-8' or C-9'), 140.8 (C-6 or C-7 or C-8' or C-9'), 140.5 (C-6 or C-7 or C-8' or C-9'), 136.2 (C-9), 135.8 (C-8a), 132.6 (C-10'), 131.5 (C-4a) 130.9 (C-7'), 130.0 (C-14'), 128.8 (C-4a'), 123.8 (C-13'), 123.3 (C-13), 122.9 (C-11'), 121.1 (C-8a'), 118.4 (C-1), 116.8 (C-5), 115.2 (C-8), 114.2, C-13), 108.4 (C-5'), 68.9 (C-1), 61.5 (C-1'), 56.9 (C-6'-OMe and C-12-OMe), 51.8 (C-3), 46.0 (C-3'), 42.6 (C—N2-Me), 42.4 (C-α'), 42.0 (C—N2'-Me), 41.6 (C-α), 28.1 (C-4), 24.6 (C-4').

HRMS-ESI (m/z) calculated for $C_{36}H_{37}N_2O_5$ [M+H]$^+$: 577.2697; Found: 577.2698.

O-Methylcocsoline (3)

(3)

$^1$H NMR (500 MHz, CDCl$_3$) δ 7.55 (1H, dd, J=8.3 Hz, J=2.1 Hz, H-14'), 7.25 (1H, dd, J=8.3 Hz, J=2.7 Hz, H-13'), 7.14 (1H, dd, J=8.3 Hz, J=2.1 Hz, H-10'), 6.91 (3H, m, H-11', H-13, H-14), 6.65 (1H, s, H-5), 6.64 (1H, d, J=1.9 Hz, H-10), 6.35 (H, s, H-5'), 6.21 (1H, s, H-8), 4.00 (1H, m, H-1'), 3.99 (3H, s, 12-OMe), 3.88 (3H, s, 6'-OMe), 3.62 (1H, d, J=4.6 Hz, H-1), 3.34 (1H, d, J=14.5 Hz, H-α'), 3.20-3.11 (2H, m, H-3, H-3'), 3.03-2.90 (4H, H-3, H-3', H-4', H-α), 2.78-2.72 (2H, m, H-4, H-α), 2.66 (1H, m, H-α'), 2.63 (3H, s, N2-Me), 2.59-2.50 (2H, m, H-4, H-4').

$^{13}$C NMR (125 MHz, CDCl$_3$) δ 154.9 (C-12'), 150.2 (C-6), 147.7 (C-11), 146.2 (C-6'), 139.9 (C-6 or C-7 or C-8' or C-9'), 139.6 (C-6 or C-7 or C-8' or C-9'), 139.5 (C-6 or C-7 or C-8' or C-9'), 139.3 (C-6 or C-7 or C-8' or C-9'), 136.4 (C-8a), 134.7 (C-9), 131.7 (C-10'), 131.2 (C-4a), 129.7 (C-7'), 128.9 (C-14'), 127.6 (C4a'), 122.6 (C-13'), 122.1 (C-14), 121.5 (C-11'), 121.1 (C-8a'), 117.9 (C-10), 116.5 (C-5), 113.2 (C-8), 112.7 (C-13), 106.9 (C-5'), 60.7 (C-1 and C-1'), 56.5 (C-6'-OMe and C-12-OMe), 45.1 (C-3'), 44.1 (C-α), 43.2 (C-3), 42.4 (C—N2-Me), 41.7 (C-α'), 29.0 (C-4), 24.3 (C-4').

HRMS-ESI (m/z) calculated for $C_{35}H_{35}N_2O_5$ [M+H]$^+$: 563.2540; Found: 563.2544.

Cocsuline (4)

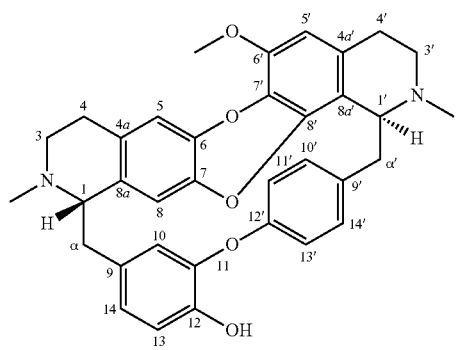

(4)

¹H NMR (500 MHz, CDCl$_3$) δ 7.58 (1H, dd, J=8.5 Hz, J=2.0 Hz, H-14'), 7.16 (2H, m, H-10', H-13'), 6.96 (1H, dd, J=8.2 Hz, J=2.4 Hz, H-11'), 6.88 (1H, d, J=8.2 Hz, H-13), 6.79 (1H, dd, J=8.3 Hz, J=2.0 Hz, H-14), 6.60 (1H, s, H-5), 6.52 (1H, d, J=2.0 Hz, H-10), 6.30 (1H, s, H-5'), 6.11 (1H, s, H-8), 3.98 (1H, t, J=2.9 Hz, H-1'), 3.84 (3H, s, 6'-OMe), 3.32 (1H, dd, J=15.0 Hz, J=2.5 Hz, H-α'), 3.22 (1H, t, J=2.9 Hz, H-1), 3.16 (1H, m, H-3'), 2.95-2.82 (4H, m, H-3, H-3', H-4', H-α), 2.76-2.59 (5H, H-3, H-4, H-4', H-α, H-α'), 2.57 (3H, s, N2'-Me), 2.49 (1H, m, H-4'), 2.39 (3H, s, N2-Me).

¹³C NMR (125 MHz, CDCl$_3$) δ 154.0 (C-12'), 148.2 (C-11), 146.3 (C-6'), 143.9 (C-12), 140.6 (C-9'), 139.8 (C-6 or C-7 or C-8'), 139.7 (C-6 or C-7 or C-8'), 139.6 (C-6 or C-7 or C-8'), 135.5 (C-8a), 134.8 (C-9), 131.5 (C-10'), 130.2 (C-4a), 129.7 (C-7'), 128.8 (C-14'), 127.5 (C-4a'), 122.7 (C-10'), 122.6 (C-14), 121.6 (C-11'), 120.5 (C-8a'), 116.9 (C-10), 115.9 (C-5), 115.7 (C-13), 114.2 (C-8), 106.7 (C-5'), 67.7 (C-1), 60.8 (C-1'), 56.5 (C-6'-OMe), 50.7 (C-3), 45.2 (C-3'), 42.9 (C—N2-Me), 42.4 (C-α'), 42.1 (C—N2'-Me), 41.3 (C-α), 27.9 (C-4), 23.6 (C-4').

HRMS-ESI (m/z) calculated for C$_{35}$H$_{35}$N$_2$O$_5$ [M+H]⁺: 563.2540; Found: 563.2543.

2'-Norcosuline (5)

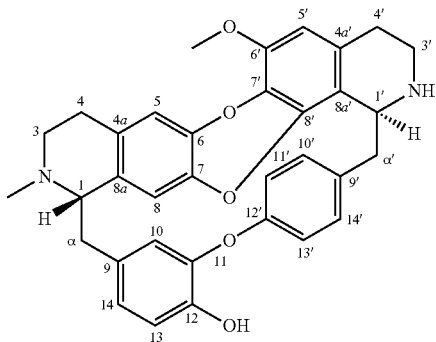

(5)

¹H NMR (500 MHz, CDCl$_3$) δ 7.61 (1H, dd, J=8.3 Hz, J=1.8 Hz, H-14'), 7.14 (2H, m, H-10', H-13'), 6.95 (1H, dd, J=8.3 Hz, J=2.6 Hz, H-11'), 6.87 (1H, d, J=8.1 Hz, H-13), 6.77 (1H, dd, J=8.1 Hz, J=2.0 Hz, H-14), 6.58 (1H, s, H-5), 6.48 (1H, d, J=1.8 Hz, H-10), 6.28 (1H, s, H-5'), 6.11 (1H, s, H-8), 4.32 (1H, t, J=3.2 Hz, H-1'), 3.84 (3H, s, 6'-OMe), 3.28 (1H, m, H-α'), 3.25 (1H, m, H-1), 3.12-3.20 (1H, m, H-3'), 2.92 (1H, dd, J=Hz, J=Hz, H-α), 2.79-2.86 (2H, m, H-3, H-α'), 2.53-2.75 (6H, H-3, H-4', H-4, H-α), 2.42 (3H, s, N2-Me).

¹³C NMR (125 MHz, CDCl$_3$) δ 154.1 (C-12'), 148.4 (C-11), 146.3 (C-6'), 144.0 (C-12), 140.6 (C-9'), 139.8 (C-6 or C-7), 139.6 (C-6 or C-7), 139.1 (C-8'), 135.9 (C-8a), 134.8 (C-9), 131.5 (C-10'), 129.9 (C-4a'), 129.8 (C-4a), 128.4 (C-14'), 128.4 (C-7'), 122.7 (C-14), 122.4 (C-13'), 122.0 (C-8a'), 121.5 (C-11'), 116.9 (C-10), 115.9 (C-5 and C-13), 114.3 (C-8), 106.9 (C-5'), 67.7 (C-1), 56.5 (C-6'-OMe), 54.3 (C-1'), 49.8 (C-3), 45.0 (C-α'), 43.1 (C—N2-Me), 41.4 (C-α), 38.9 (C-3'), 28.5 (C-4'), 27.8 (C-4).

HRMS-ESI (m/z) calculated for C$_{34}$H$_{33}$N$_2$O$_5$ [M+H]⁺: 549.2384; Found: 549.2383

Cocsoline (6)

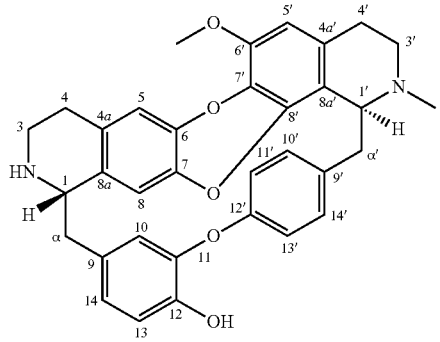

(6)

¹H NMR (500 MHz, MeOD) δ 7.55 (1H, dd, J=8.5 Hz, J=2.0 Hz, H-14'), 7.20 (1H, dd, J=8.5 Hz, J=2.6 Hz, H-13'), 7.10 (1H, dd, J=8.2 Hz, J=2.1 Hz, H-10'), 6.85 (2H, m, H-13, H-14), 6.79 (1H, dd, J=8.4 Hz, J=2.5 Hz, H-11'), 6.58 (1H, s, H-5), 6.57 (1H, d, J=1.8 Hz, H-10), 6.49 (1H, s, H-5'), 6.22 (1H, s, H-8), 3.95 (1H, d, J=3.8 Hz, H-1'), 3.83 (3H, s, 6'-OMe), 3.52 (1H, d, J=5.9 Hz, H-1), 3.31 (1H, m, H-α'), 3.31 (1H, m, H-3'), 3.02 (1H, m, H-3), 2.94 (3H, m, H-3, H-3', H-4'), 2.85 (1H, m, H-α), 2.74 (2H, m, H-4, H-α), 2.67-2.59 (3H, m, H-4, H-4', H-α'), 2.56 (3H, s, N2'-Me).

¹³C NMR (125 MHz, MeOD) δ 157.5 (C-12'), 149.9 (C-11), 148.0 (C-6'), 146.8 (C-12), 141.3 (C-6 or C-7), 140.7 (C-6 or C-7), 140.3 (C-8'), 139.9 (C-9'), 137.2 (C-8a), 134.3 (C-9), 133.0 (C-4a), 132.7 (C-10'), 130.9 (C-7'), 130.1 (C-14'), 128.6 (C-4a'), 124.2 (C-14), 123.4 (C-13'), 122.2 (C-11'), 121.3 (C-8a'), 119.7 (C-10), 118.2 (C-13), 117.1 (C-5), 114.2 (C-8), 108.6 (C-5'), 62.0 (C-1'), 61.3 (C-1), 56.9 (C-6'-OMe), 45.5 (C-3'), 43.8 (C-3), 43.2 (C-α), 42.2 (C-α' and C—N2-Me), 29.1 (C-4), 24.7 (C-4').

HRMS-ESI (m/z) calculated for C$_{34}$H$_{33}$N$_2$O$_5$ [M+H]⁺: 549.2384; Found: 549.2381.

Nortrilobine (7)

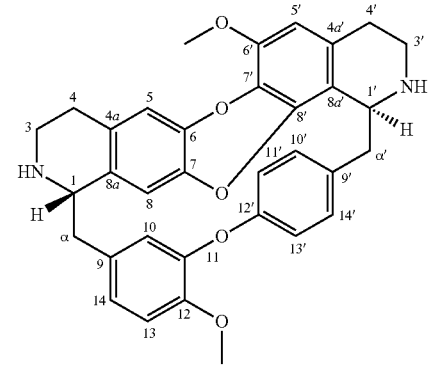

(7)

¹H NMR (500 MHz, MeOD) δ 7.58 (1H, dd, J=8.4 Hz, J=2.2 Hz, H-14'), 7.20 (1H, dd, J=8.3 Hz, J=2.6 Hz, H-13'), 7.07 (1H, dd, J=8.3 Hz, J=2.2 Hz, H-10'), 7.04 (1H, d, J=8.4 Hz, H-13), 7.02 (1H, dd, J=8.3 Hz, J=2.0 Hz, H-14), 6.74 (1H, dd, J=8.4 Hz, J=2.5 Hz, H-11'), 6.62 (1H, s, H-5), 6.61 (1H, d, J=1.8 Hz, H-10), 6.57 (1H, s, H-5'), 6.27 (1H, s, H-8), 4.37 (1H, dd, J=5.8 Hz, J=1.5 Hz, H-1'), 3.91 (3H, s, 12-OMe), 3.80 (1H, m, H-1), 3.79 (3H, s, 6'-OMe), 3.45-3.34 (3H, m, H3', H-α'), 3.19 (1H, m, H-3), 3.12-2.98 (H-3, H-4', Hα), 2.93-2.88 (3H, m, H-4', H-α, H-α'), 2.83 (1H, m, H-4), 2.71 (1H, m, H-4).

¹³C NMR (125 MHz, MeOD) δ 157.3 (C-12'), 151.3 (C-11), 149.8 (C-12), 148.7 (C-6'), 142.0 (C-6 or C-7), 141.0 (C6 or C-7), 139.9 (C-8'), 138.4 (C-9'), 133.8 (C-9), 133.5 (C-8a), 132.7 (C-4a and C-10'), 130.9 (C-7'), 130.5 (C-14'), 128.6 (C-4a'), 124.2 (C-14), 123.6 (C-13'), 122.3 (C-11'), 119.6 (C-10), 119.2 (C-8a'), 117.2 (C-5), 114.8 (C-13), 114.6 (C-8), 108.9 (C-5'), 59.7 (C-1), 57.0 (C-6'-OMe or C-12-OMe), 56.9 (C-6'-OMe or C-12-OMe), 54.3 (C-1'), 44.2 (C-α'), 42.6 (C-3), 40.8 (C-α), 38.2 (C-3'), 27.6 (C-4), 26.9 (C-4').

HRMS-ESI (m/z) calculated for $C_{34}H_{33}N_2O_5$ [M+H]⁺: 549.2384; Found: 549.2388

1,2-Dehydroapateline (8)

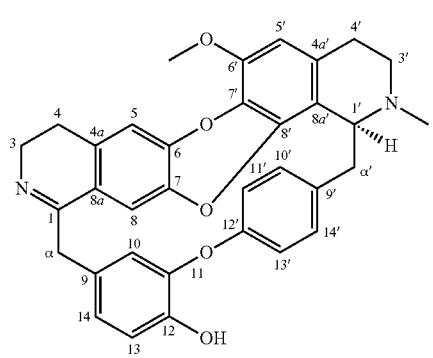

(8)

¹H NMR (500 MHz, MeOD) δ 7.44 (1H, d, J=7.6 Hz, H-14'), 7.22 (1H, dd, J=7.8 Hz, J=1.8 Hz, H-13'), 6.90 (1H, d, J=7.8 Hz, H-10'), 6.75 (2H, m, H-13, H-14), 6.70 (2H, m, H-8, H-11'), 6.60 (1H, d, J=1.6 Hz, H-10), 6.58 (1H, s, H-5), 6.57 (1H, s, H-5'), 3.97 (1H, d, J=9.9, H-1'), 3.93 (1H, dd, J=13.3 Hz, J=2.3 Hz, H-α), 3.83 (3H, s, 6'-OMe), 3.73 (1H, m, H-3), 3.42 (1H, d, J=13.3 Hz, H-α), 3.31 (1H, m, H-3'), 3.25 (1H, d, J=12.5 Hz, H-α'), 3.19 (1H, m, H-3), 2.99 (1H, m, H-4'), 2.87 (2H, m, H-3', H-4'), 2.75 (1H, m, H-α'), 2.54 (3H, s, N2'-Me), 2.42 (1H, m, H-4), 2.29 (1H, m, H-4).

¹³C NMR (125 MHz, MeOD) δ 169.0 (C-1), 155.9 (C-12'), 149.0 (C-12), 148.2 (C-6'), 146.5 (C-11), 144.6 (C-7), 140.2 (C-6), 139.6 (C-8'), 137.7 (C-9'), 136.8 (C-4a), 132.7 (C-10'), 131.6 (C-14'), 130.1 (C-4a'), 129.7 (C-7'), 129.2 (C-9), 124.4 (C-8a), 124.3 (C-13'), 123.8 (C-14), 122.4 (C-11'), 120.0 (C-8a'), 119.1 (C-10), 177.7 (C-13), 116.3 (C-5 and C-8), 109.3 (C-5'), 60.2 (C-1'), 56.8 (C-6'-OMe), 47.1 (C-3), 45.4 (C-3'), 42.2 (C—N2'Me), 42.5 (C-α), 40.8 (C-α'), 26.2 (C-4), 25.2 (C-4').

HRMS-ESI (m/z) calculated for $C_{34}H_{31}N_2O_5$ [M+H]⁺: 547.2227; Found: 547.2214.

1,2-Dehydroapateline (9)

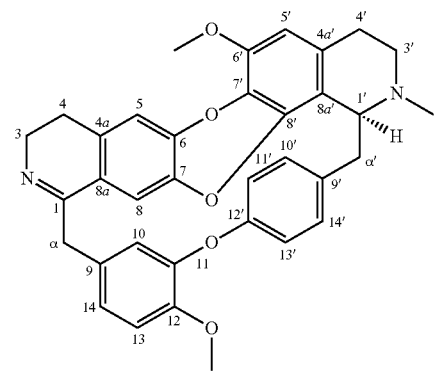

(9)

¹H NMR (500 MHz, MeOD) δ 7.45 (1H, d, J=7.0 Hz, H-14'), 7.20 (1H, dd, J=8.4 Hz, J=2.2 Hz, H-13'), 6.93 (1H, d, J=8.4 Hz, H-13), 6.89 (2H, m, H-10', H-14), 6.77 (1H, s, H-8), 6.69 (1H, dd, J=8.2 Hz, J=2.2 Hz, H-11'), 6.67 (1H, d, J=2.2 Hz, H-10), 6.64 (1H, s, H-5), 6.60 (1H, s, H-5'), 4.04 (1H, d, J=13.1 Hz, J=2.2 Hz, H-α), 3.98 (1H, d, J=9.4 Hz, H-1'), 3.85 (6H, s, 6'-OMe, 12-OMe), 3.77 (1H, m, H-3), 3.45 (1H, d, J=13.2 Hz, H-α), 3.33 (1H, m, H-3'), 3.25 (1H, dd, J=12.6 Hz, J=1.0 Hz, H-α'), 3.20 (1H, m, H-3), 2.99 (1H, m, H-4'), 2.89 (2H, m, H-3', H-4'), 2.75 (1H, m, H-α'), 2.53 (3H, s, N2'-Me), 2.49 (1H, m, H-4), 2.33 (1H, m, H-4).

¹³C NMR (125 MHz, MeOD) δ 169.0 (C-1), 155.7 (C-12'), 150.4 (C-11), 149. (C-12), 148.2 (C-6'), 144.6 (C-7), 140.3 (C-6), 139.6 (C-8'), 137.8 (C-9'), 136.8 (C-4a), 132.7 (C-10'), 131.7 (C-14'), 130.7 (C-9), 130.2 (C-4a'), 129.7 (C-7'), 124.5 (C-8a), 124.3 (C-13'), 123.7 (C-14), 122.3 (C-11'), 120.0 (C-8a'), 118.9 (C-10), 116.3 (C-5 and C-8), 114.3 (C-13), 109.4 (C-5'), 60.2 (C-1'), 56.9 (C-6'-OMe and C-12-OMe), 47.2 (C-3), 45.4 (C-3'), 42.6 (C—N2'Me), 42.4 (C-α), 40.7 (C-α'), 26.3 (C-4), 25.2 (C-4').

HRMS-ESI (m/z) calculated for $C_{35}H_{33}N_2O_5$ [M+H]⁺: 561.2384; Found: 561.2376.

Example II. Biological Tests of the Compounds According to the Invention

II.1. CMV-luc Reexpression

Aiming at identifying new DNMT inhibitors, plant extract samples were tested for their ability to reactivate gene expression upon use of an integrated luciferase reporter system under the control of a methylated CMV promoter in leukemia KG-1 cells which inhibits its expression (CMV-luc assay reported in following Table). Among the hits of interest, an alkaloidic extract from *Cocculus hirsutus* induced luciferase expression. The extract was fractionated by preparative HPLC. Identification of the active components was accomplished by HRMS and NMR spectroscopy. The pure compounds isolated from the extract through bio-guided fractionation are trilobine and bisbenzylisoquinoline analogue products. The active compounds were then further evaluated for their ability to inhibit DNMTs in vitro and DNA methylation in cancer cells.

KG-1 cells were stably transfected with the firefly luciferase reporter gene (luc+ from pGL3; Promega) under the control of the cytomegalovirus (CMV) promoter (from pEGFP-N1; Clontech Laboratories Inc.) partially methylated (50%). 20,000 cells per well were seeded in a 96-well plate. After 24 hour incubation in the presence of the test compound or solvent (DMSO), the induction of the promoter was measured by quantification of the luciferase signal with the Brite-lite assay system (PerkinElmer) according to the manufacturer's protocol. The luminescence was measured on an EnVision multilabel plate reader (PerkinElmer), and the data are expressed as the fold induction as compared with the DMSO control. The mean of three experiments and the standard error is reported.

Compounds of the invention induced expression of the luciferase gene under the control of the methylated CMV promoter.

TABLE 2

Induction fold of the luciferase expression

Reactivation fold of luciferase gene reporter
In KG-1 CMV-Luc
Concentration (μM)

| Cpd | | 10 | 5 | 3.2 | 1 | 0.5 | 0.32 | 0.1 |
|---|---|---|---|---|---|---|---|---|
| 1 | Trilobine | cyt. tox. | 6.4 ± 0.1 | 3.5 ± 1.1 | 2.6 ± 1.4 | 1.6 ± 0.8 | 1.9 ± 1.2 | 1.1 ± 0.1 |
| 2 | Isotrilobine | 6.1 ± 0.5 | 3.1 ± 0.6 | 2.4 ± 0.7 | 3.6 ± 2.9 | 2.8 ± 0.8 | 2.4 ± 1.4 | 1.0 ± 0.1 |
| 5 | 2'-Norcocsuline | cyt. tox. | 5.1 ± 0.1 | 3.9 ± 0.4 | 2.6 ± 1.6 | 2.1 ± 0.6 | 2.3 ± 0.7 | 1.0 ± 0.2 |
| 7 | Nortrilobine | cyt. tox.. | 12.3 ± 1.2 | 5.4 ± 2.6 | 2.6 ± 1.8 | 1.9 ± 1.3 | 1.7 ± 0.5 | 1.1 ± 0.2 |

II.2. hDNMT3A Assay.

hDNMT3A enzyme inhibition was adapted from the restriction-based fluorescence assay protocol as described in the literature (Ceccaldi et al. *ChemBioChem* 2011, 12, 1337-1345). Briefly, a 5'-labelled biotin oligonucleotide is hybridized to its complementary strand labelled with 6-carboxyfluorescein at the 3'-end into a 384 well microplate (black Optiplates; Perkin Elmer) pre-coated with avidin. The duplex contains a unique CpG site overlapping with a restriction site of a methylation sensitive restriction enzyme. The human C-terminal DNMT3A (a.a. 623-908), produced as described in the literature (Gros et al. *Nucl. Acids Res.* 2013, 41(19):e185), was added in each well (200 ng/well) and mixed with the chemical compounds at desired concentrations and freshly prepared AdoMet (20 μM final concentration) to start the reaction in a total volume of 50 μL. After 1 hour incubation at 37° C. each well were washed three times with PBS, Tween-20 0.05%, NaCl (500 mM) and three more times with PBST. Specific fluorescent signals were detected with the methylation-sensitive restriction enzyme HpyCH4IV (NEB) as described and measured on a Perkin Elmer Envision detector. The percentage of inhibition is reported. The formula used to calculate the percentage of inhibition is $[(X-Y)/X] \times 100$, where X is the signal determined in the absence of the inhibitor and Y is the signal obtained in the presence of the inhibitor. The concentration at which 50% of efficacy of inhibition is observed (EC50) was determined by analysis of a concentration range of the tested compound in triplicates. The non-linear regression fittings with sigmoidal dose-response (variable slope) were performed with GraphPad Prism 4.03 (GraphPad Software).

Compounds of the invention inhibit human DNMT3A enzyme.

TABLE 3 hDNMT3A inhibition.

| | | | hDNMT 3A inhibition | |
|---|---|---|---|---|
| | | | Inhibition (%) | |
| Cpd | | EC50 (μM)* | 32 μM | 10 μM |
| 1 | Trilobine | 3.8 [3.2 to 4.4] | 94 | 78 |
| 2 | Isotrilobine | 6.8 [5.6 to 8.3] | 76 | 56 |
| 3 | O-Methylcocsoline | 4.6 [4.0 to 5.2] | 100 | 95 |
| 4 | Cocsuline | >10 | 66 | 23 |
| 5 | 2'-Norcocsuline | 5.5 [2.9 to 10] | 88 | 73 |
| 6 | Cocsoline | >10 | 91 | 37 |
| 7 | Nortrilobine | 4.3 [3.0 to 3.6] | 94 | 83 |
| 8 | 1,2-Dehydroapateline | >10 | 68 | 41 |
| 9 | 1,2-Dehydrotelobine | >10 | 63 | 37 |

*95% confidence interval

II.3. hDNMT1 Assay.

His-DNMT1 (182 kDa, human) was cloned, expressed and purified as described in the literature (Halby et al. *ChemBioChem* 2012, 13, 157-165). The reaction was performed in a 104 total reaction volume in low volume NBS™ 384-well microplates (Corning), containing the tested compound (up to 1% DMSO), 1 μM of a SAM/[methyl-$^3$H] SAM (3 TBq/mmol, PerkinElmer) mix in a ratio of 3-to-1 (isotopic dilution 1*:3), 0.3 μM of biotinylated hemimethylated DNA duplex (5'-GATmCGCmCGATGmCGmC-GAATmCGmCGATmCGATGmCGAT-3' and BIOT-5'-ATCGCATCGATCGCGATTCGCGCATCGGCGATC-3'), and 90 nM of DNMT1 in methylation buffer (20 mM HEPES pH 7.2, 1 mM EDTA, 50 mM KCl, 25 μg/mL BSA). The reaction was incubated at 37° C. for 2 hours. 8 μL, are then transferred into a streptavidin 96-well scintillant coated Flashplate™ (PerkinElmer) containing 190 μL of 20 μM SAH in 50 mM Tris-HCl pH 7.4. The Flashplate™ was agitated at room temperature for 1 hour and read in 200 μL of 50 mM Tris-HCl pH 7.4 on TopCount NXT (PerkinElmer). The percentage of inhibition is reported. The formula used to calculate the percentage of inhibition is $[(X-Y)/X] \times 100$, where X is the signal determined in the absence of the inhibitor and Y is the signal obtained in the presence of the inhibitor.

Compounds of the invention inhibit human DNMT1 enzyme. At 32 μM, the percentage of inhibition was 50% for Trilobine (compound 1), and 99% for Nortrilobine (compound 7).

Since the compounds are inhibitors of DNMTs and are able to induce luciferase expression, we evaluated the ability of compound 1 (Trilobine) to demethylate the CMV promoter in the cancer cells and to open the chromatin on such promoter.

II.4 CMV Promoter Analysis: Nucleosome Occupancy and DNA Methylation Profile

Using the Nucleosome Occupancy and Methylome Sequencing (NOMe-Seq) technique, the methylation status of the CMV promoter and the position of the nucleosomes on such promoter were both analysed.

NOMe-seq is a modified version of the methylation-dependent single promoter assay described by Miranda et al. (*Curr Protoc Mol Biol.* 2010 21.17.1-16) and the methylase-based DNA assay was performed as previously described with minor modifications (Hochedlinger K, Plath K 2009; Sharma et al. 2010, You et al. 2011, Kelly et al. 2012). After nuclei extraction, GpC methyltransferase (M.CviPI; New England Biolabs) reactions were done in M.CviPI reaction buffer. GpC methyltransferase treatment was followed by DNA extraction, sodium bisulfite conversion, PCR amplification of the region of interest, cloning, and sequencing of individual clones to reveal the structure of single replicas as functional units. After treatment with the compounds or with DMSO, KG-1 Luc cells were centrifuged for 5 min at 500×g. Cell pellets were washed in ice-cold PBS, resuspended in 1 mL of ice-cold nuclei buffer [10 mM Tris (pH 7.4), 10 mM NaCl, 3 mM $MgCl_2$, 0.1 mM EDTA, and 0.5% Nonidet P-40, plus protease inhibitors] per $2\times10^6$ cells, and incubated on ice for 10 min. Nuclei were recovered by centrifugation at 900×g for 5 min, washed twice in nuclei wash buffer [10 mM Tris (pH 7.4), 10 mM NaCl, mM $MgCl_2$, and 0.1 mM EDTA containing protease inhibitors], and resuspended with 200 μL in 1× M.CviPI reaction buffer supplemented with 0.3 M sucrose, 160 μL SAM (New England Biolabs). 100 μL of purified genomic DNA were treated with 100 U of M.CviPI for 15 min at 37° C. in 200 μL final volume. The other part of 100 μL of purified genomic DNA were not treated with 100 U of M.CviPI but just incubated for 15 min at 37° C. to obtain CpG methylation profile. Reactions were stopped by the addition of an equal volume of stop solution [20 mM Tris.HCl (pH 7.9), 600 mM NaCl, 1% SDS, 10 mM EDTA, and 400 μg/mL Proteinase K] and incubated at 55° C. overnight. DNA was purified by phenol/chloroform extraction and ethanol precipitation. Bisulfite conversion was performed with the EZ DNA Methylation-Gold Kit (Zymo Research). Bisulfited DNA was eluted with 12 μL of water and 8 μL were used for CMV amplification.

PCR Amplification of Bisulfite-Treated DNA

The CMV promoter DNA amplification was carried on 8.3 μL eluted bisulfited DNA in 20 μL PCR reaction containing 1× KAPA2G Buffer A, 2.0 mM $MgCl_2$, 200 μM dNTPs, 125 nM each primer and 1.0 units KAPA2G™ Robust HotStart DNA Polymerase (KapaBiosystems) on C1000 Touch™ thermal cycler 95° C. 3 min following by 95° C. for 20 sec, 55° C. for 30 sec, 72° C. for 30 sec×40 cycles and final extension at 72° C. 1 min. PCR fragments were quality controlled by agarose gel electrophoresis. Oligonucleotides used are listed in the following Table.

Steps of cloning and sequencing were as those described previously except that M13 PCR was used to amplify the cloned sequence in 20 μL PCR reaction volume containing 1× KAPA2G Buffer B, 2.0 mM $MgCl_2$, 200 μL dNTPs, 125 nM each primer and 1.0 U KAPA2G™ Robust HotStart DNA Polymerase (KapaBiosystems) on C1000 Touch™ thermal cycler 95° C. 3 min following by 95° C. for 20 sec, 55° C. for 30 sec, 72° C. for 30 sec×40 cycles and final extension at 72° C. 1 min.

TABLE 4

Oligonucleotides used in this study.

| Targets | Sequences | Analysis |
|---|---|---|
| CMV | F: GGGGTTATTAGTTTATAGTTTATATATGGA<br>R: AATACCAAAACAAACTCCCATTAAC | NOMeSeq |
| M13 forward | 5' TGTAAAACGACGGCCAGT 3' | NOMeSeq |
| P16 CDKN2A | F: GGTTTTTTTAGAGGATTTGAGGGATAGG<br>R: CTACCTAATTCCAATTCCCCTACAAACTTC | COBRA |
| P15 CDKN2B | F: TGAGATGGTAGAATAAAAATTATTAAAAA<br>R: AAACAAAAACATACCCAATAAAAAC | Bisulfite PCR Cloning-Sequencing |
| P16 CDKN2A | F: CATGGAGCCTTCGGCTGACT<br>R: CCATCATCATGACCTGGATCG | RT-qPCR |
| YWHAZ | F: CCCTCAAACCTTGCTTCTAGGAGA<br>R: TCATATCGCTCAGCCTGCTCG | RT-qPCR |
| TBP | F: TTGACCTAAAGACCATTGCACTTCGT<br>R: TTACCGCAGCAAACCGCTTG | RT-qPCR |

Sequence Alignment and Analysis of CG and GC Methylation Levels

Genomic alignment and bisulfite sequence analysis was performed largely as previously described (Berman et al. *Nat Genet* 2012, 44, 40-6).

BISMA (Bisulfite Sequencing DNA Methylation Analysis) software was used for CpG methylation analysis of primary bisulfite sequencing data from subcloned individual molecules (Rohde et al. *BMC Bioinformatics* 2010, 11, 230). Red symbols are indicative of a methylated cytosine in a CpG, while blue (CG) symbols represent unmethylated cytosines in a CpG. Methyl Viewer (Pardo et al., 2011 *Nucleic Acids Res* 2011, 39, e5) was used to obtain GC methylation results and nucleosome occupancy. Black symbols represented a methylated cytosine in a GpC and white symbols represent non methylated cytosines in a GpC. The ratio of methylation is representative of the chromatin accessibility by M.CviPI and nucleosome occupancy. The combined methylation status for each clone by CpG (BISMA) or GpC (Methyl Viewer) site has been assembled. The methylation status of cytosines in CpG and GpC contexts at a given position within the sequence, given as ratio of methylation, can be calculated as follows: R=[MCT/MCNT], where MCT is the percentage of Methylated Cytosines analysed DNA sequence in the Treated sample, and MCNT is the percentage of Methylated Cytosines on the same DNA sequence in a Non Treated sample.

C5 DNA Methylation Analysis at Endogenous Promoters

Cancer cell lines (colon HCT116 or leukaemia KG1) were treated with the compounds as indicated in the Data Tables and then analysed as following.

DNA Extraction and Bisulphite Treatment

DNA was isolated from cultured cells using the DNeasy Blood and Tissue Kit according to the manufacturer's specifications (Qiagen). DNA bisulphite conversion was performed on 2 μg of DNA using the EZ DNA Methylation- Gold Kit according to the manufacturer's specifications (Zymo Research) and bisulfited DNA was eluted with 10 μL of water. Two different techniques were used to analyse the DNA methylation profile after bisulfite conversion of genomic DNA: (A) cloning and sequencing or (B) COBRA. The primers for each promoter are specified in the Table 3.

A/Cloning and Sequencing

Sequencing of bisulfite-treated DNA allowing resolution of the methylation state of every cytosine in the target sequence, at single molecule resolution, is considered as the "gold standard" for DNA methylation analysis.

CDKN2B Promoter PCR Amplification of Bisulfite-Treated DNA

Bisulfite-specific primers with a minimum length of 18 bp were designed using Primer 3 program. The target sequence of the designed primers contained no CpGs allowing amplification of both un- and hypermethylated DNAs. All primers were tested for their ability to yield high quality sequences and primers that gave rise to an amplicon of the expected size using non-bisulfite treated DNA as a template were discarded, thus ensuring the specificity for bisulfite-converted DNAs. Primers used in this study are listed in the above Table. The targeted DNA amplification was set up with 2.5 μL eluted bisulfited DNA in 50 μL PCR reaction volume containing 1×PCR buffer, 1.5 mM MgCl$_2$, 200 μM dNTPs, 200 nM each primer and 1.0 units Platinum® Taq DNA Polymerase (Invitrogen) on C1000 Touch™ thermal cycler 94° C. 2 min following by 94° C. for 30 sec, 55° C. for 30 sec, 72° C. for 1 min×35 cycles and final extension at 72° C. 6 min. PCR fragments were quality controlled by agarose gel electrophoresis.

Cloning and Sequencing

PCR amplicons were cloned with the StrataClone Ultra Blunt PCR Cloning Kit (Agilent Technologies), according to the manufacturers' instructions and up to 24 clones were picked for sequencing. First, M13 PCR was performed to amplify cloned sequence: each colony was resuspended in 50 μL water and 1 μL of each bacterial suspension was used to a 20 μL PCR reaction volume containing 1×PCR buffer, 2.5 mM MgCl$_2$, 2 mM dNTPs, 3.2 μM each primer that anneals to sites flanking the insertion/ligation plasmid site, and 1.25 units AmpliTaq Gold DNA polymerase (Applied Biosystems) on C1000 Touch™ thermal cycler 95° C. 10 min following by 95° C. for 45 sec, 55° C. for 45 sec, 72° C. for 1 min×35 cycles and final extension at 72° C. 10 min. PCR amplicons were cleaned up using Bio-Gel-P100 (Bio-Rad Laboratories) to remove any excess nucleotides and primers. Final sequencing was performed using a M13 primer on ABI 3100 capillary sequencers using ⅛ dilution of ABI Prism BigDye terminator V3.1 sequencing chemistry after hotstart 96° C. for 60 seconds and thermocycling 96° C. for 10 sec, 50° C. for 10 sec, 60° C. for 4 min×25 cycles. Sequencing reactions were cleaned up using Sephadex® G-50 (GE Healthcare) to remove any excess nucleotides and dyes. Electrophoregram files and methylation signals at a given CpG site were quantified using the BISMA software as described in the literature (Rohde et al. *BMC Bioinformatics* 2010, 11, 230).

B/Combined Bisulfite Restriction Analysis (COBRA)

This technique is a variation of bisulfite sequencing, and combines bisulfite conversion based polymerase chain reaction with restriction digestion. DNA methylation levels are easily and quickly measured without the need for laborious and costing more time sub-cloning and sequencing, as with bisulfite sequencing.

CDKN2A Promoter PCR Amplification of Bisulfite-Treated DNA

DNA amplification was set up with 100 ng eluted bisulfited DNA in 50 μl PCR reaction containing 1×PCR buffer, 2.5 mM MgCl$_2$, 0.3 mM dNTPs, 400 nM each primer and 1.25 units EpiTaq HS (Takara) on C1000 Touch™ thermal cycler by 98° C. for 10 sec, 55° C. for 30 sec, 72° C. for 30 sec×40 cycles. 20 μL of PCR amplicons were digested in 30 μL by 2 units of BsiEI at 60° C. for 90 min. DNA fragments were migrated by 2% agarose gel electrophoresis and each band was quantified by Image Lab Software v2.0 (BioRad Laboratories).

Compound 1 of the invention is able to demethylate the CMV promoter in the cancer cells and to open the chromatin on such promoter.

TABLE 5

Activity of compound 1 on the CMV promoter and P15 promoter in leukaemia KG1 cells and on P16 promoter and expression in colon cancer cells HCT116

| | KG1 CMV-Luc model (24 h) at 5 μM | | Demethylation (COBRA) at 100 nM | | Rexpression (RT qPCR) at 100 nM P16/HCT116 expression fold to non-treated cells at 3 days |
|---|---|---|---|---|---|
| | FI-24 h | DNA demethylation | Chromatin accessibility | P16/HCT116 | P15/KG1 | |
| Trilobine compound 1 | 5.8 ± 0.6 | −37 ± 8% | 1.9 ± 0.1 | −37% after 3 days (at 0.1 μM) −52% after 7 days (at 0.1 μM) −53% after 21 days (at 0.1 μM) | −25% after 3 days (at 0.32 μM) | 5.0 ± 2.14 |

II.5 Anti-Proliferative Activity 8 human cancer cells were obtained from the ATCC (USA) and cultivated in medium suggested by the supplier supplemented with foetal calf serum (Lonza, France), at 37° C. and under 5% CO$_2$. To measure the anti-proliferative properties of tested molecules, 2×10$^4$ cells are seeded at day 0 in a 96 wells plate. The compounds to be tested, stored at −20° C. as 10$^{-2}$ M stock solution in 100% DMSO, are freshly diluted on day 1 in the cell medium, before adding a dose range of 3.2 nM to 10 μM to the cells. The cell viability is assessed using the ATPLite kit from Perkin (ATPlite 1 Step Luminescence Assay System, ref 3016739), following the provider instructions. The raw data are analyzed with GraphPad Prism software (v4.03) to generate IC50 values corresponding to the compound concentrations giving 50% reduction in cell viability. The values presented are the mean results of at least two independent experiments. The standard errors are indicated.

Compound 1 of the invention present a potential anti-cancer activity on a panel of cancer cell lines: IC50 of compound 1 ranged from 0.9 to 6.8 µM.

TABLE 6

Antiproliferative activity of Compound 1 on cancer cell lines

| Cell line | Cancer type | $EC_{50}$ (µM) |
| --- | --- | --- |
| SKOV-3 | Ovarian | 1.8 [0.74 to 4.5]* |
| KM-12 | Colorectal | 1.6 [0.67 to 3.7]* |
| HOP-62 | Lung | 1.7 [0.89 to 3.4]* |
| Colo-205 | Colorectal | 2.6 [2.0 to 3.3]* |
| TK10 | Kidney | 2.5 [2.3 to 2.7]* |
| HCT-116 | Colorectal | 1.2 +/− 0.2 |
| KG-1 | Leukaemia | 2.2 +/− 0.8 |
| Karpass299 | Lymphoma | 1.3 +/− 0.7 |

*95% confidence intervalle

To further test the effect of compound 1 on DNA methylation and gene reexpression, its effect on the invasiveness capacity of metastatic melanoma WM266 cell line was analysed in a 3D model.

II. 6 Spheroid Formation and Invasion Assay

After treatment with compound 1 at concentrations at which the compound is not cytotoxic, metastatic melanoma cells WM-266-4 GFP (3000 cells/condition) were allowed to form spheroids for 2 days on agarose 1% (Sigma-Aldrich, #A95-39) coated in 96-well plates, leading to ~300 µm diameter spheroids. Then six different spheroids for each condition were individually embedded in EMEM media (Lonza, #BE12-684F) containing 1% of Bovin Collagen I (BD, #354231) and 2% SVF. The initial spheroid size and the 24 h invasion area were measured by fluorescent microscopy, using an Axiovert 200M device (5× Plan-Neofluor objective, Carl Zeiss, Germany). Fluorescent invasion areas were quantified using Image J (NIH) software on the sum of six Z-stacks images (20 µm interval) for each spheroid. Invasion Index was obtained by normalising the invasion area at 24 hours by the initial spheroid area. Six individual spheroids were quantified for each condition and three independent experiments were performed. The corresponding results are represented in the FIGURE.

Compound 1 of the invention decrease the invasion index in metastatic melanoma cells.

In conclusion, the compounds inhibit DNA methylation, in vitro and in cancer cells. By their action, the compounds are able to reprogram the cancer cells towards less aggressive state and could be used to sensitize towards immunotherapies and chemotherapies.

The invention claimed is:

1. A method for the treatment of a cancer comprising the administration to a person in need thereof of an effective dose of a compound selected from trilobine and its natural triple-bridged bisbenzylisoquinoline alkaloidal analogues, wherein trilobine and its natural triple-bridged bisbenzylisoquinoline alkaloidal analogues correspond to the following formula (I):

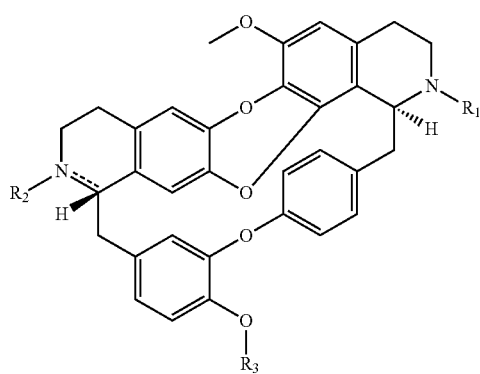

(I)

wherein:
= represents a double or single bond, and
when = represents a single bond $R_1$, $R_2$ and $R_3$ represent, independently of each other, a hydrogen atom or a methyl group, at least one of said radicals $R_1$, $R_2$ and $R_3$ being a methyl group,
when = represents a double bond $R_1$ and $R_3$ are, independently of each other, a hydrogen atom or a methyl group and $R_2$ is absent,
or a pharmaceutically acceptable salt or solvate thereof, and
wherein the cancer is a cancer over-expressing DNA methyl transferase (DNMT).

2. The method according to claim 1, wherein:
when $R_2$ is a methyl group, both $R_1$ and $R_3$ are hydrogen atoms, and
when $R_2$ is a hydrogen atom, at least one of $R_1$ and $R_3$ is a hydrogen atom.

3. The method according to claim 1, wherein trilobine and its natural triple-bridged bisbenzylisoquinoline alkaloidal analogues are selected from the group consisting of trilobine, isotrilobine, O-methylcocsoline, cocsuline, 2'-norcocsuline, cocsoline, nortrilobine, 1,2-dehydroapateline, 1,2-dehydrotelobine and the pharmaceutically acceptable salts and solvates thereof.

4. The method according to claim 1, wherein the cancer is selected from colon cancer; hepatocarcinoma; melanoma; breast cancer; ovarian cancer; kidney cancer; liver cancer; pancreatic cancer; prostate cancer; glioblastoma; lung cancer; neuroblastoma; myofibroblastic tumor; lymphoma; leukemia; and multiple myeloma.

5. The method according to claim 4, wherein the lung cancer is a non-small cell lung cancer; the lymphoma is a B- or T-cell lymphoma or an anaplastic large-cell lymphoma; and the leukemia is an acute myeloid leukemia (AML), a myelodysplastic syndrome (MDS), a chronic myelomonocytic leukemia (CMML) or a chronic myeloid leukemia (CML).

6. A method for inhibiting DNA methyl transferase (DNMT) comprising the administration to a person in need thereof of an effective dose of a compound selected from trilobine and its natural triple-bridged bisbenzylisoquinoline alkaloidal analogues, wherein trilobine and its natural triple-bridged bisbenzylisoquinoline alkaloidal analogues correspond to the following formula (I):

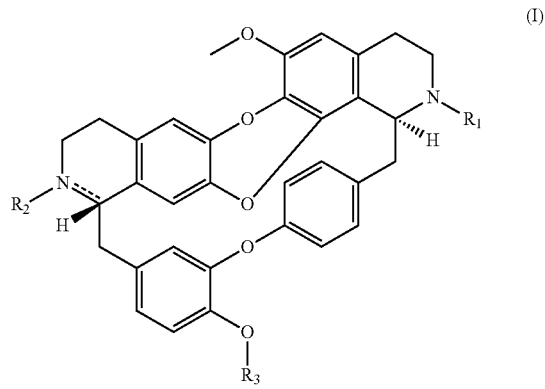

(I)

wherein:
= represents a double or single bond, and
when = represents a single bond $R_1$, $R_2$ and $R_3$ represent, independently of each other, a hydrogen atom or a methyl group, at least one of said radicals $R_1$, $R_2$ and $R_3$ being a methyl group,
when = represents a double bond $R_1$ and $R_3$ are, independently of each other, a hydrogen atom or a methyl group and $R_2$ is absent,
or a pharmaceutically acceptable salt or solvate thereof.

7. The method according to claim 6, wherein:
when $R_2$ is a methyl group, both $R_1$ and $R_3$ are hydrogen atoms, and
when $R_2$ is a hydrogen atom, at least one of $R_1$ and $R_3$ is a hydrogen atom.

8. The method according to claim 6, wherein trilobine and its natural triple-bridged bisbenzylisoquinoline alkaloidal analogues are selected from the group consisting of trilobine, isotrilobine, O-methylcocsoline, cocsuline, 2'-norcocsuline, cocsoline, nortrilobine, 1,2-dehydroapateline, 1,2-dehydrotelobine and the pharmaceutically acceptable salts and solvates thereof.

9. A method for the treatment of cancer comprising the simultaneous, separate or sequential administration to a person in need thereof of an effective dose of a pharmaceutical product comprising:
at least one compound selected from trilobine and its natural triple-bridged bisbenzylisoquinoline alkaloidal analogues, and
at least another active ingredient,
wherein trilobine and its natural triple-bridged bisbenzylisoquinoline alkaloidal analogues correspond to the following formula (I):

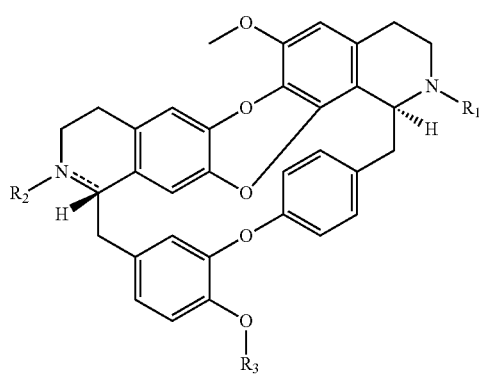

(I)

wherein:
═══ represents a double or single bond, and
when ═══ represents a single bond $R_1$, $R_2$ and $R_3$ represent, independently of each other, a hydrogen atom or a methyl group, at least one of said radicals $R_1$, $R_2$ and $R_3$ being a methyl group,
when ═══ represents a double bond $R_1$ and $R_3$ are, independently of each other, a hydrogen atom or a methyl group and $R_2$ is absent,
or a pharmaceutically acceptable salt or solvate thereof, and
wherein the cancer is a cancer over-expressing DNA methyl transferase (DNMT).

10. The method according to claim 9, wherein trilobine and its natural triple-bridged bisbenzylisoquinoline alkaloidal analogues are selected from the group consisting of trilobine, isotrilobine, O-methylcocsoline, cocsuline, 2'-norcocsuline, cocsoline, nortrilobine, 1,2-dehydroapateline, 1,2-dehydrotelobine and the pharmaceutically acceptable salts and solvates thereof.

11. The method according to claim 9, wherein the at least another active ingredient is an anticancer agent.

12. The method according to claim 9, wherein the cancer is selected from colon cancer; hepatocarcinoma; melanoma; breast cancer; ovarian cancer; kidney cancer; liver cancer; pancreatic cancer; prostate cancer; glioblastoma; lung cancer; myofibroblastic tumor; lymphoma; leukemia; and multiple myeloma.

13. The method according to claim 12, wherein the lung cancer is a non-small cell lung cancer; the lymphoma is a B- or T-cell lymphoma or an anaplastic large-cell lymphoma; and the leukemia is an acute myeloid leukemia (AML), a myelodysplastic syndrome (MDS), a chronic myelomonocytic leukemia (CMML) or a chronic myeloid leukemia (CML).

14. A method for the treatment of a cancer comprising the administration to a person in need thereof of an effective dose of a pharmaceutical composition comprising at least one compound selected from trilobine and its natural triple-bridged bisbenzylisoquinoline alkaloidal analogues, and at least pharmaceutically acceptable excipient,
wherein trilobine and its natural triple-bridged bisbenzylisoquinoline alkaloidal analogues correspond to the following formula (I):

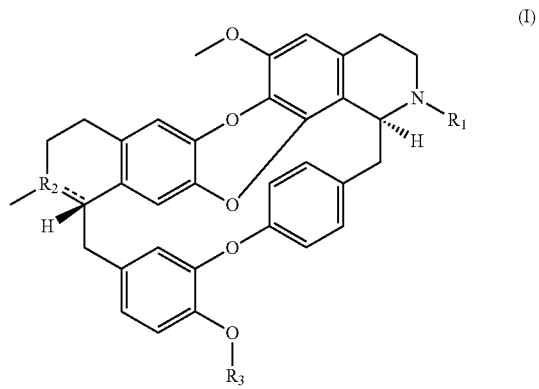

(I)

wherein:
═══ represents a double or single bond, and
when ═══ represents a single bond $R_1$, $R_2$ and $R_3$ represent, independently of each other, a hydrogen atom or a methyl group, at least one of said radicals $R_1$, $R_2$ and $R_3$ being a methyl group,
when ═══ represents a double bond $R_1$ and $R_3$ are, independently of each other, a hydrogen atom or a methyl group and $R_2$ is absent,
or a pharmaceutically acceptable salt or solvate thereof, and
wherein the cancer is a cancer over-expressing DNA methyl transferase (DNMT).

15. The method according to claim 14, wherein trilobine and its natural triple-bridged bisbenzylisoquinoline alkaloidal analogues are selected from the group consisting of trilobine, isotrilobine, O-methylcocsoline, cocsuline, 2'-norcocsuline, cocsoline, nortrilobine, 1,2-dehydroapateline, 1,2-dehydrotelobine and the pharmaceutically acceptable salts and solvates thereof.

* * * * *

UNITED STATES PATENT AND TRADEMARK OFFICE
CERTIFICATE OF CORRECTION

PATENT NO. : 10,517,863 B2
APPLICATION NO. : 15/765040
DATED : December 31, 2019
INVENTOR(S) : Yoann Menon et al.

Page 1 of 2

It is certified that error appears in the above-identified patent and that said Letters Patent is hereby corrected as shown below:

In the Claims

At Column 30, Line 20 (Claim 14):
Change:

"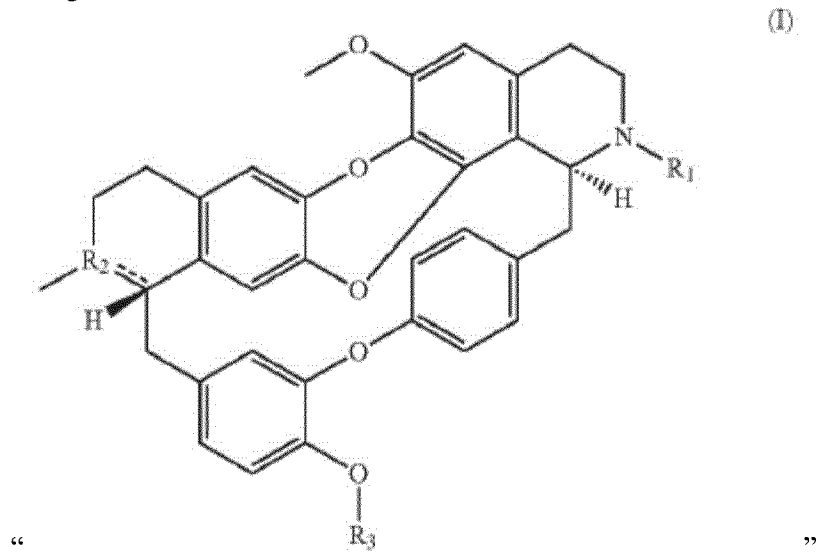"

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,517,863 B2

To:

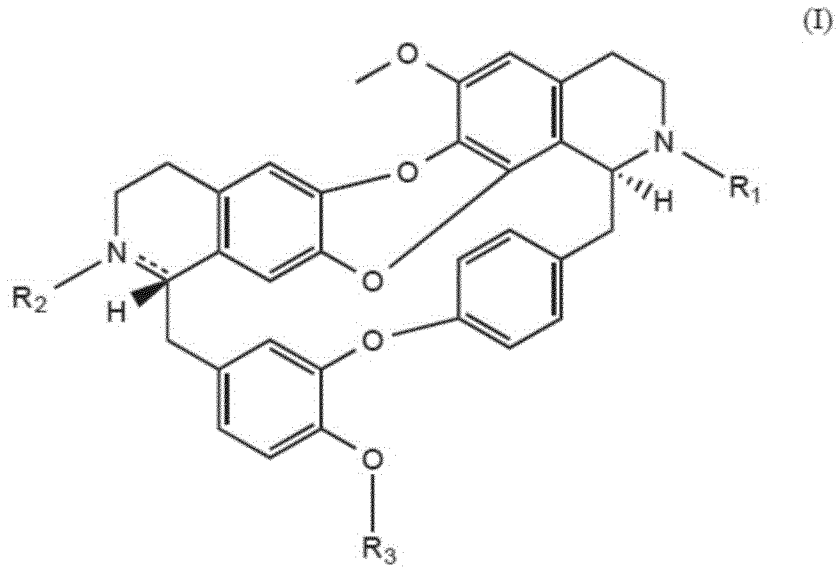

-- --

SEQUENCE LISTING

```
<160> NUMBER OF SEQ ID NOS: 15

<210> SEQ ID NO 1
<211> LENGTH: 33
<212> TYPE: DNA
<213> ORGANISM: Artificial Sequence
<220> FEATURE:
<223> OTHER INFORMATION: Biotinylated hemimethylated DNA duplex
<220> FEATURE:
<221> NAME/KEY: modified_base
<222> LOCATION: (4)..(4)
<223> OTHER INFORMATION: methylCytosine
<220> FEATURE:
<221> NAME/KEY: modified_base
<222> LOCATION: (7)..(7)
<223> OTHER INFORMATION: methylCytosine
<220> FEATURE:
<221> NAME/KEY: modified_base
<222> LOCATION: (12)..(12)
<223> OTHER INFORMATION: methylCytosine
<220> FEATURE:
<221> NAME/KEY: modified_base
<222> LOCATION: (14)..(14)
<223> OTHER INFORMATION: methylCytosine
<220> FEATURE:
<221> NAME/KEY: modified_base
<222> LOCATION: (19)..(19)
<223> OTHER INFORMATION: methylCytosine
<220> FEATURE:
<221> NAME/KEY: modified_base
<222> LOCATION: (21)..(21)
<223> OTHER INFORMATION: methylCytosine
<220> FEATURE:
<221> NAME/KEY: modified_base
<222> LOCATION: (25)..(25)
<223> OTHER INFORMATION: methylCytosine
<220> FEATURE:
<221> NAME/KEY: modified_base
<222> LOCATION: (30)..(30)
<223> OTHER INFORMATION: methylCytosine

<400> SEQUENCE: 1
gatcgccgat gcgcgaatcg cgatcgatgc gat                                33
```

```
<210> SEQ ID NO 2
<211> LENGTH: 33
<212> TYPE: DNA
<213> ORGANISM: Artificial Sequence
<220> FEATURE:
<223> OTHER INFORMATION: Biotinylated hemimethylated DNA duplex
<220> FEATURE:
<221> NAME/KEY: misc_binding
<222> LOCATION: (1)..(1)
<223> OTHER INFORMATION: Biotinylation

<400> SEQUENCE: 2
atcgcatcga tcgcgattcg cgcatcggcg atc                                    33

<210> SEQ ID NO 3
<211> LENGTH: 30
<212> TYPE: DNA
<213> ORGANISM: Artificial Sequence
<220> FEATURE:
<223> OTHER INFORMATION: CMV forward primer

<400> SEQUENCE: 3
ggggttatta gtttatagtt tatatatgga                                        30

<210> SEQ ID NO 4
<211> LENGTH: 25
<212> TYPE: DNA
<213> ORGANISM: Artificial Sequence
<220> FEATURE:
<223> OTHER INFORMATION: CMV reverse primer

<400> SEQUENCE: 4
aataccaaaa caaactccca ttaac                                             25

<210> SEQ ID NO 5
<211> LENGTH: 18
<212> TYPE: DNA
<213> ORGANISM: Artificial Sequence
<220> FEATURE:
<223> OTHER INFORMATION: M13 forward primer

<400> SEQUENCE: 5
tgtaaaacga cggccagt                                                     18

<210> SEQ ID NO 6
<211> LENGTH: 28
<212> TYPE: DNA
<213> ORGANISM: Artificial Sequence
<220> FEATURE:
<223> OTHER INFORMATION: P16 CDKN2A forward primer

<400> SEQUENCE: 6
ggttttttta gaggatttga gggatagg                                          28

<210> SEQ ID NO 7
<211> LENGTH: 30
<212> TYPE: DNA
<213> ORGANISM: Artificial Sequence
<220> FEATURE:
<223> OTHER INFORMATION: P16 CDKN2A reverse primer

<400> SEQUENCE: 7
ctacctaatt ccaattcccc tacaaacttc                                        30

<210> SEQ ID NO 8
<211> LENGTH: 29
<212> TYPE: DNA
```

```
<213> ORGANISM: Artificial Sequence
<220> FEATURE:
<223> OTHER INFORMATION: P15 CDKN2B forward primer

<400> SEQUENCE: 8
tgagatggta gaataaaaat tattaaaaa                                29

<210> SEQ ID NO 9
<211> LENGTH: 25
<212> TYPE: DNA
<213> ORGANISM: Artificial Sequence
<220> FEATURE:
<223> OTHER INFORMATION: P15 CDKN2B reverse primer

<400> SEQUENCE: 9
aaacaaaaac atacccaata aaaac                                   25

<210> SEQ ID NO 10
<211> LENGTH: 20
<212> TYPE: DNA
<213> ORGANISM: Artificial Sequence
<220> FEATURE:
<223> OTHER INFORMATION: P16 CDKN2A forward primer

<400> SEQUENCE: 10
catggagcct tcggctgact                                         20

<210> SEQ ID NO 11
<211> LENGTH: 21
<212> TYPE: DNA
<213> ORGANISM: Artificial Sequence
<220> FEATURE:
<223> OTHER INFORMATION: P16 CDKN2A reverse primer

<400> SEQUENCE: 11
ccatcatcat gacctggatc g                                       21

<210> SEQ ID NO 12
<211> LENGTH: 24
<212> TYPE: DNA
<213> ORGANISM: Artificial Sequence
<220> FEATURE:
<223> OTHER INFORMATION: YWHAZ forward primer

<400> SEQUENCE: 12
ccctcaaacc ttgcttctag gaga                                    24

<210> SEQ ID NO 13
<211> LENGTH: 21
<212> TYPE: DNA
<213> ORGANISM: Artificial Sequence
<220> FEATURE:
<223> OTHER INFORMATION: YWHAZ reverse primer

<400> SEQUENCE: 13
tcatatcgct cagcctgctc g                                       21

<210> SEQ ID NO 14
<211> LENGTH: 26
<212> TYPE: DNA
<213> ORGANISM: Artificial Sequence
<220> FEATURE:
<223> OTHER INFORMATION: TBP forward primer

<400> SEQUENCE: 14
ttgacctaaa gaccattgca cttcgt                                  26
```

```
<210> SEQ ID NO 15
<211> LENGTH: 20
<212> TYPE: DNA
<213> ORGANISM: Artificial Sequence
<220> FEATURE:
<223> OTHER INFORMATION: TBP reverse primer

<400> SEQUENCE: 15
ttaccgcagc aaaccgcttg                                              20
```